United States Patent [19]

Lantzsch

[11] Patent Number: 5,574,165
[45] Date of Patent: Nov. 12, 1996

[54] PROCESS FOR THE PREPARATION OF CYANOIMINO-1,3-THIAZOLIDINES

[75] Inventor: Reinhard Lantzsch, Wuppertal, Germany

[73] Assignee: Bayer Aktiengesellschaft, Leverkusen, Germany

[21] Appl. No.: 506,937

[22] Filed: Jul. 26, 1995

[30] Foreign Application Priority Data

Aug. 4, 1994 [DE] Germany .......................... 44 27 569.2

[51] Int. Cl.⁶ .................................................. C07D 277/04
[52] U.S. Cl. ........................................... 548/198; 564/248
[58] Field of Search .................... 564/248, 198; 548/198

[56] References Cited

U.S. PATENT DOCUMENTS 4,616,025 10/1986 Ezer et al. .............................. 514/342

OTHER PUBLICATIONS

R. Neidlein, et al., Archiv der Pharmazie, vol. 305, pp. 731 and 735, (1972).
J. Zimtek, et al., Org. Prep. Proc., vol. 23, No. 6, pp. 721–728, (1991).
G. E. Robinson, Chem. and Ind., pp. 349–352, (1983).
R. L. Webb, et al., J. Hetercyclic Chem., vol. 24, pp. 275–278, (1987).

Neidlein, et al., Chemical Abstracts, abstract No. 29657r, vol. 78, No. 5, p. 494, (1973).

*Primary Examiner*—Johann Richter
*Assistant Examiner*—Laura R. Cross
*Attorney, Agent, or Firm*—Sprung Horn Kramer & Woods

[57] ABSTRACT

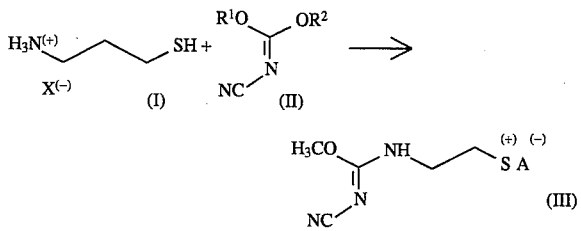

cyclized at pH 8 to 9.5 to give cyanoimino-1,3-diazolidine of the formula

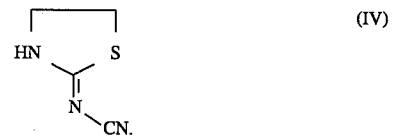

in which
  $R^1$ and $R^2$ are lower alkyl,
  X is an acid radical, and
  A is a metal ion or an equivalent ammonium ion.

3 Claims, No Drawings

PROCESS FOR THE PREPARATION OF CYANOIMINO-1,3-THIAZOLIDINES

The invention relates to a novel process for the preparation of cyanoimino-1,3-thiazolidine.

It is known that cyanoimino-1,3-thiazolidine is obtained if dimethyl N-cyanodithiocarbonate and cysteamine are heated at reflux in ethanol (cf. Archiv der Pharmazie 305, 731 (1972). This process, however, has the disadvantage that two equivalents of methyl mercaptan are eliminated. Industrial production by this route is therefore very costly on toxicological and environmental grounds, since methyl mercaptan is a severe respiratory poison, necessitates additional safety measures, and must either be incinerated or destroyed by oxidation with aqueous sodium hypochlorite solution or hydrogen peroxide.

It is also known that cyanoimino-1,3-thiazolidine is obtained if dimethyl N-cyanoimidocarbonate is stirred for a prolonged period at a pH of 10–11 with cysteamine in aqueous sodium hydroxide solution (cf. Org. Prep. Procedure Int. 23, (6), 721–728 (1991). The melting point of the product thus obtained (m.p. 168°–170° C.), however, differs considerably from that of pure cyanoimino-1,3-thiazolidine (m.p. 154°–156° C.), since the former is probably contaminated by secondary products.

Therefore, further purification would reduce still further the yield, which is indicated as being 48%, so that this process is also unsuitable for industrial production.

Surprisingly it has now been found that cyanoimino-1,3-thiazolidine is obtained in a very good yield and purity if cysteamine salts of the formula (I)

$$H_3N^+\diagdown\diagup SH \quad (I)$$

in which

X represents an acid radical are reacted in the presence of a diluent, in the presence of at least 2 equivalents of base and, if desired, in the presence of a protective-gas atmosphere with dialkyl N-cyanoimidocarbonates of the formula (II)

$$\begin{array}{c} R^1O \diagdown \diagup OR^2 \\ \| \\ N \\ NC \diagup \end{array} \quad (II)$$

in which $R^1$ and $R^2$ represent methyl, ethyl, n-propyl, isopropyl, n-butyl, isobutyl, sec-butyl or tert-butyl to give the intermediate product of the formula (III)

$$\begin{array}{c} H_3CO \diagdown \diagup NH \diagdown \diagup \\ \| \\ N \\ NC \diagup \end{array} \quad S^{(-)} A^{(+)} \quad (III)$$

in which $A^{(+)}$ represents a metal ion equivalent or an ammonium ion which is subsequently cyclized at a pH of from 8 to 9.5 to give cyanoimino-1,3-thiazolidine of the formula (IV)

$$\begin{array}{c} HN \quad\quad S \\ \diagdown \diagup \\ N \\ \diagdown CN \end{array} \quad (IV)$$

It must be regarded as extremely surprising that the cyanoimino-1,3-thiazolidine is obtained in high purity and yield by the process according to the invention, since it is known that, in the reaction of dimethyl N-cyanoimidocarbonate with cysteamine in water at 0° C., either methyl N-cyano-N'-(2-mercaptoethyl)-carbamimidate or the disulphide compound which results therefrom is formed [cf. Chemistry and Industry 1983, 349–352; Org. Prep. Procedures Int. 23, (6) 721–728 (1991)]. The novel process therefore represents a substantial improvement over the prior art.

For the process according to the invention, it is preferred to employ compounds of the formula (I) in which X represents an acid radical such as, for example, halogen, acetate, sulphate or hydrogen sulphate.

For the process according to the invention, it is furthermore preferred to employ compounds of the formula (II) in which $R^1$ and $R^2$ represent methyl or ethyl.

In the intermediate of the formula (III) which is formed in the course of the process according to the invention, it is preferred if A represents a sodium, potassium or ammonium ion.

Using, for example, cysteamine hydrochloride, sodium hydroxide solution and dimethyl N-cyanoimidocarbonate, the process according to the invention can be described by the following formula scheme.

1st stage $$H_3N^+\diagdown\diagup SH + \begin{array}{c} H_3CO \diagdown \diagup OCH_3 \\ \| \\ N \\ NC \diagup \end{array} \xrightarrow{NaOH}$$

$$Na^{(+)}S^{(-)}\diagdown\diagup \begin{array}{c} NH \diagdown \diagup OCH_3 \\ \| \\ N \\ NC \diagup \end{array}$$

2nd stage $$Na^{(+)}S^{(-)}\diagdown\diagup \begin{array}{c} NH \diagdown \diagup OCH_3 \\ \| \\ N \\ NC \diagup \end{array} \xrightarrow{H^{(+)}}$$

$$\begin{array}{c} HN \quad\quad S \\ \diagdown \diagup \\ N \\ \diagdown CN \end{array}$$

The cysteamine salts of the formula (I) and the dialkyl N-cyanoimidocarbonates of the formula (II) to be used as starting materials in the process according to the invention are generally known compounds of organic chemistry.

The process according to the invention is preferably carried out in the presence of a diluent. Suitable diluents are all common solvents which are inert under the reaction conditions. These include, for example, water, alcohols such as, for example, methanol, ethanol, propanol or butanol; nitriles such as, for example, acetonitrile, butyronitrile or isobutyronitrile, or ethers such as, for example, dimethoxyethane, methyl tert-butyl ether or TAME. It is particularly preferred to carry out the reaction in water or a water/alcohol mixture.

When carrying out the process according to the invention the reaction temperatures can be varied within a relatively wide range. The process is in general carried out at temperatures of between 0° C. and 100° C., preferably at temperatures of between 0° C. and 70° C.

The process according to the invention is carried out in such a way that the appropriate cysteamine salt of the formula (I) is initially introduced in a mixture of a base and one of the abovementioned solvents, and then one of the dialkyl N-cyanoimidocarbonates of the formula (II) is added in portions at the temperature indicated. Cyclization is then brought about at a pH of between 8 and 9.5 by addition of a mineral acid, for example sulphuric acid or hydrochloric acid, which if desired may also be employed in the form of a gas. The reverse addition is also possible: the dialkyl N-cyanoimidocarbonate is initially introduced in a solvent, and a solution of the cysteamine salt with at least 2 equivalents of base is metered in. In this procedure, the formation of unwanted disulphide is particularly small. The reaction mixture can be worked up by conventional methods (cf. preparation example).

Suitable bases are alkali metal hydroxides such as, for example, sodium hydroxide and potassium hydroxide, alkaline earth metal hydroxides such as, for example, calcium hydroxide, and alkali metal carbonates and alkali metal alcoholates such as sodium carbonate, potassium carbonate, sodium methylate, potassium methylate, sodium ethylate and potassium ethylate, which are employed in excess.

The process according to the invention is carded out if desired in the presence of an inert gas. A suitable inert gas in this context is nitrogen, and also virtually all noble gases, especially argon.

The cyanoimino-1,3-thiazolidine prepared by the process according to the invention can be used as a starting substance for the production of pesticides (cf. EP-A 235 725).

The invention is illustrated by the following example.

EXAMPLE 1

17.8 g (0.2 mol) of 45% strength sodium hydroxide solution is initially introduced under a nitrogen atmosphere and is diluted with 30 ml of water, and 11.6 g (0.1 mol) of cysteamine hydrochloride are added. The solution is stirred at 30°–35° C. for 15 minutes and then cooled to 0° C.

Then 11.4 g (0.1 mol) of dimethyl N-cyanoimidocarbonate are added in portions and the mixture is stirred at 0°–5° C. for 2.5 hours. The pH is 12.7. The temperature is allowed to rise to room temperature and the pH is adjusted to 9.5 by addition of hydrochloric acid, and then the mixture is heated to 40° C. and the pH is adjusted to 9.0.

The reaction mixture is stirred for 8 hours, the pH is adjusted to 6.8 and the solid is filtered off with suction and dried.

10.9 g of cyanoimino-1,3-thiazolidine of melting point 154° C. are obtained. The purity according to HPLC is 95.8%. The content of disulphide is 1.9%; this corresponds to a yield of 82.1% of theory.

I claim:
1. Process for the preparation of cyanoimino-1,3-thiazolidine, characterized in that cysteamine salts of the formula (I)

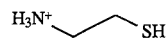

in which

X represents an acid radical are reacted in the presence of a diluent, in the presence of at least 2 equivalents of base and, if desired, in the presence of a protective-gas atmosphere with dialkyl N-cyanoimidocarbonates of the formula (II)

in which $R^1$ and $R^2$ represent methyl, ethyl, n-propyl, isopropyl, n-butyl, isobutyl, sec-butyl or tert-butyl to give the intermediate product of the formula (III)

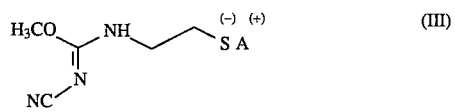

in which $A^{(+)}$ represents a metal ion equivalent or an ammonium ion which is subsequently cyclized at a pH of from 8 to 9.5 to give cyanoimino-1,3-thiazolidine of the formula (IV)

2. Process according to claim 1, characterized in that compounds of the formula (I) are employed in which X represents an acid radical from the group halogen, acetate, sulphate or hydrogen sulphate.

3. Process according to claim 2, characterized in that compounds of the formula (II) are employed in which $R^1$ and $R^2$ represent methyl or ethyl.

* * * * *